(12) United States Patent
Kaneko et al.

(10) Patent No.: US 9,148,554 B2
(45) Date of Patent: Sep. 29, 2015

(54) IMAGE PICKUP UNIT FOR ENDOSCOPE AND ENDOSCOPE

(71) Applicant: OLYMPUS CORPORATION, Tokyo (JP)

(72) Inventors: Tomohisa Kaneko, Hino (JP); Takahiko Mitani, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/048,125

(22) Filed: Oct. 8, 2013

(65) Prior Publication Data

US 2014/0078276 A1    Mar. 20, 2014

Related U.S. Application Data

(63) Continuation of application No. PCT/JP2013/059297, filed on Mar. 28, 2013.

(30) Foreign Application Priority Data

Apr. 25, 2012    (JP) .................................. 2012-100253

(51) Int. Cl.
    *A62B 1/04*      (2006.01)
    *H04N 5/225*     (2006.01)
    *G02B 23/24*     (2006.01)
    *A61B 1/00*      (2006.01)
    *A61B 1/045*     (2006.01)
        (Continued)

(52) U.S. Cl.
    CPC .......... *H04N 5/2254* (2013.01); *A61B 1/00009* (2013.01); *A61B 1/00096* (2013.01); *A61B 1/00179* (2013.01); *A61B 1/045* (2013.01); *A61B 1/051* (2013.01); *G02B 23/243* (2013.01); *G02B 23/2476* (2013.01); *G02B 23/2484* (2013.01); *G02B 23/26* (2013.01)

(58) Field of Classification Search
    None
    See application file for complete search history.

(56) References Cited

U.S. PATENT DOCUMENTS 5,521,639 A * 5/1996 Tomura et al. ................. 348/243
7,042,487 B2 * 5/2006 Nakashima ..................... 348/65
(Continued)

FOREIGN PATENT DOCUMENTS

CN   101164495 A    4/2008
EP   0 568 216 A1   11/1993
(Continued)

OTHER PUBLICATIONS

Extended Supplementary European Search Report dated Feb. 4, 2015 from related European Application No. 13 78 2480.1.

*Primary Examiner* — Sath V Perungavoor
*Assistant Examiner* — Dakshesh Parikh
(74) *Attorney, Agent, or Firm* — Scully, Scott, Murphy & Presser, PC (57) ABSTRACT

In this invention, an image pickup unit for endoscope including an image pickup device includes, in an optical black region of the image pickup device, a phase reference pixel region in which a pixel that outputs a signal capable of being used for phase adjustment of the video by receiving light is disposed, and an optical axis of an objective optical system member having an image circle which is narrower than an effective pixel region of the image pickup device is arranged at a position closer to the phase reference pixel region with respect to a center of the effective pixel region such that light transmitted through the objective optical system member can reach the phase reference pixel region.

4 Claims, 7 Drawing Sheets

(51) Int. Cl.
*A61B 1/05* (2006.01)
*G02B 23/26* (2006.01)

(56) References Cited

U.S. PATENT DOCUMENTS

2003/0081132 A1* 5/2003 Kuno et al. ............... 348/222.1
2008/0088701 A1* 4/2008 Unsai et al. ................. 348/65

FOREIGN PATENT DOCUMENTS

| EP | 1 769 719 A1 | | 4/2007 | |
|----|----|----|----|----|
| JP | 02-084930 A | | 3/1990 | |
| JP | 05-308579 A | | 11/1993 | |
| JP | 2008253789 A | * | 4/2008 | ............... A61B 1/04 |
| JP | 2008253789 A | * | 10/2008 | ............... A61B 1/04 |
| JP | 2008253789 A | * | 10/2008 | |
| JP | 2011-235021 A | | 11/2011 | |

* cited by examiner

IMAGE PICKUP UNIT FOR ENDOSCOPE AND ENDOSCOPE

CROSS REFERENCE TO RELATED APPLICATION

This application is a continuation application of PCT/JP2013/059297 filed on Mar. 28, 2013 and claims benefit of Japanese Application No. 2012-100253 filed in Japan on Apr. 25, 2012, the entire contents of which are incorporated herein by this reference.

BACKGROUND OF THE INVENTION

1. Field of the Invention

The present invention relates to an image pickup unit for endoscope including an image pickup device, and an endoscope.

2. Description of the Related Art

In medical fields and industrial fields, for example, endoscopes have been used in order to observe a region which is difficult to observe such as an inside of a living body or an inside of a construction, and such endoscopes include an insertion portion which can be introduced from outside into inside of a living body or a construction, and also includes, at the insertion portion, an image pickup unit for picking up an optical image.

An image pickup unit for endoscope includes: an objective optical system member constituted of a lens which forms an image of an object; and an image pickup device such as a CCD (charge coupled device) or a CMOS (Complementary Metal-Oxide Semiconductor) sensor disposed on an image-forming surface of the objective optical system member.

An image pickup unit for endoscope is generally configured such that the camera control unit is provided outside the insertion portion, since there is a need for reducing the size of the outer diameter of the insertion portion. Such a configuration of an image pickup apparatus provided to an endoscope is generally called as a camera head separation type image pickup apparatus or the like. In an endoscope, signal communication between the image pickup device and the camera control unit is performed through a relatively long transmission cable often and several centimeters to several meters, for example.

In such an endoscope, delay of a video signal outputted from the image pickup device to the camera control unit is likely to occur due to a variation in length of a transmission cable and a variation in electrical performances of the incorporated electronic components, for example. In order to address such a problem, it is necessary to synchronize operation of the image pickup device with operation of the camera control unit by performing video phase adjustment such as adjustment of a sampling timing with respect to a phase of a video signal using the camera control unit and other electric circuits, for example. In order to perform video phase adjustment, a method of providing a timing generator on the image pickup device side, or a method of reducing a variation in length of a transmission cable and a variation in electrical performances of incorporated electronic components can be considered, for example. However, if a timing generator is provided on the image pickup device side, the size of the electronic circuit around the image pickup device increases, which results in an increase in the diameter of the insertion portion of the endoscope. Furthermore, in order to reduce tolerances of the transmission cable and the incorporated electronic components, it is necessary to increase the sizes of the cable and the electronic components, and also in such a case, the size of the insertion portion of the endoscope increases.

Therefore, Japanese Patent Application Laid-Open Publication No. 5-308579, for example, discloses a camera head separation type image pickup apparatus in which a technology of allowing a signal as an indicator to be outputted from a predetermined pixel in an optical black region of an image pickup device and adjusting sampling timings of the camera control unit and other circuits by using the signal as the indicator, to synchronize the image pickup device and the camera control unit is disclosed.

SUMMARY OF THE INVENTION

An image pickup unit for endoscope according to one aspect of the present invention is an image pickup unit for endoscope which is provided in an insertion portion of an endoscope and includes an objective optical system member, an image pickup device, and a transmission cable, the image pickup unit for endoscope being configured to be connectable, through the transmission cable, to a camera control unit which generates a video based on a signal outputted from the image pickup device, wherein the image pickup device includes, in a pixel forming region in which a plurality of pixels are disposed, an effective pixel region, a video display region provided in the effective pixel region, and a phase reference pixel region in which a pixel that outputs a signal capable of being used for phase adjustment of the video by receiving light is disposed, the phase reference pixel region being provided outside the video display region, and the objective optical system member is configured such that an intersection point at which an optical axis of the objective optical system member intersects with the effective pixel region is arranged shifted to a position closer to the phase reference pixel region with respect to a center of the effective pixel region so as to allow light transmitted through the objective optical system member to reach the phase reference pixel region. In addition, an endoscope according to one aspect of the present invention includes the image pickup unit for endoscope.

DETAILED DESCRIPTION OF THE PREFERRED EMBODIMENTS

Hereinafter, preferred embodiments of the present invention will be described with reference to drawings. Note that, in the drawings used for the following description, a different scale size is used for each of the components in order to allow each of the components to be illustrated in a recognizable size in the drawings, and the present invention is not limited to the number, shapes, ratio of the sizes of the components, and a relative positional relationship among the components shown in these drawings.

First Embodiment

Hereinafter, one example of an embodiment of the present invention will be described. First, with reference to FIG. 1, description will be made on one example of a configuration of an endoscope 101 including an image pickup unit 1 which is an image pickup unit for endoscope according to the present invention. The endoscope 101 of the present embodiment is configured to be able to be introduced into a subject such as a human body and capable of optically picking up an image of a predetermined region to be observed in the subject. Note that a subject into which the endoscope 101 is introduced is not limited to a human body, but may be another living body, or may be an artificial material such as a machine or a construction.

Figure 1:
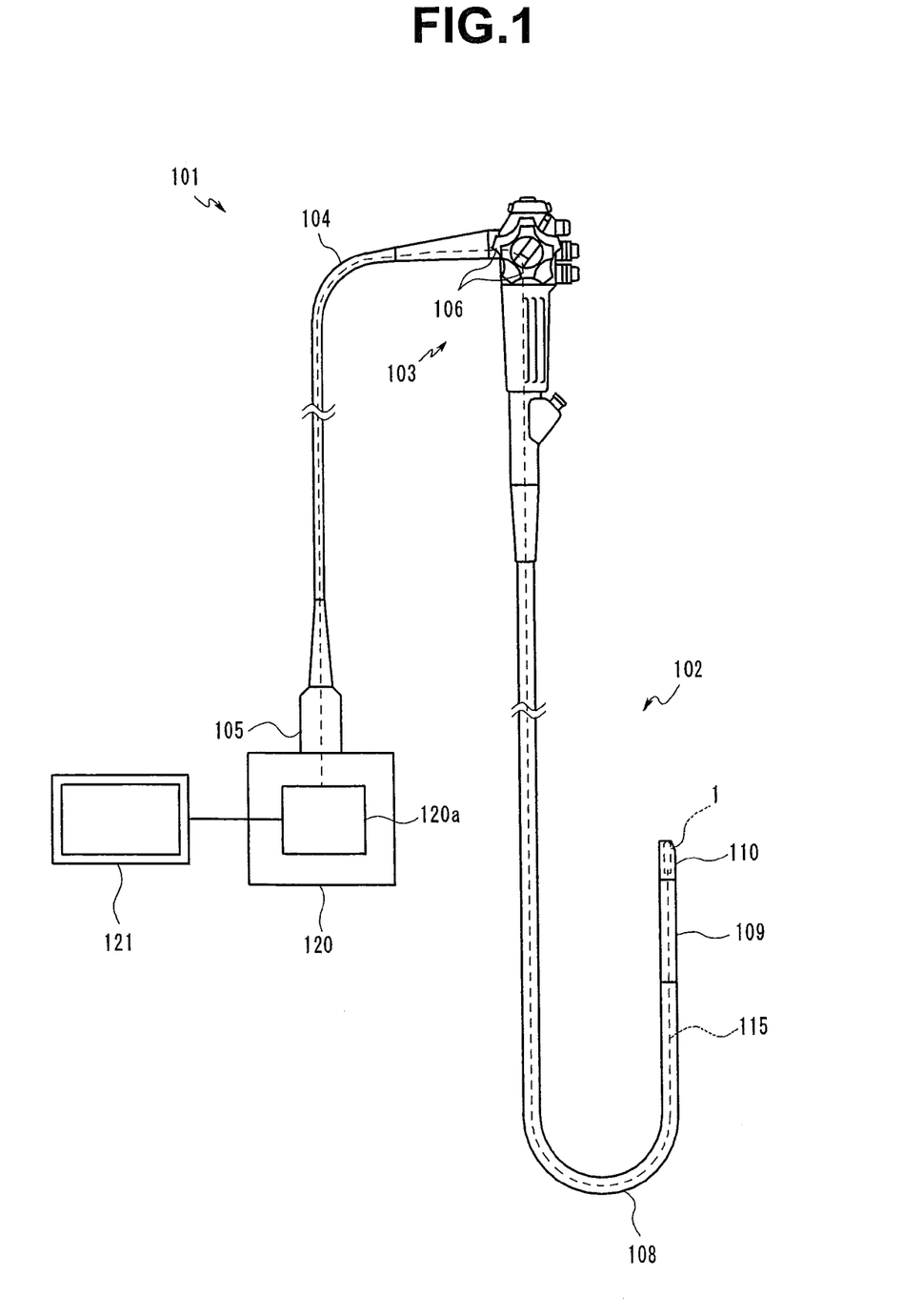
FIG. 1 is a view illustrating a configuration of an endoscope.

The endoscope 101 according to the present embodiment is mainly configured by an elongated insertion portion 102 to be introduced into inside a subject, an operation portion 103 positioned at a proximal end of the insertion portion 102, and a universal cord 104 extended from the side portion of the operation portion 103.

The insertion portion 102 is constituted of a distal end portion 110 disposed at the distal end of the insertion portion, a bendable bending portion 109 disposed on the proximal end side of the distal end portion 110, and a flexible tube portion 108 having flexibility and disposed on the proximal end side of the bending portion 109 and connected to the distal end side of the operation portion 103, which are provided in a linked manner. Note that the endoscope 101 may be what is called a rigid endoscope which does not include a region having flexibility in the insertion portion.

Figure 2:
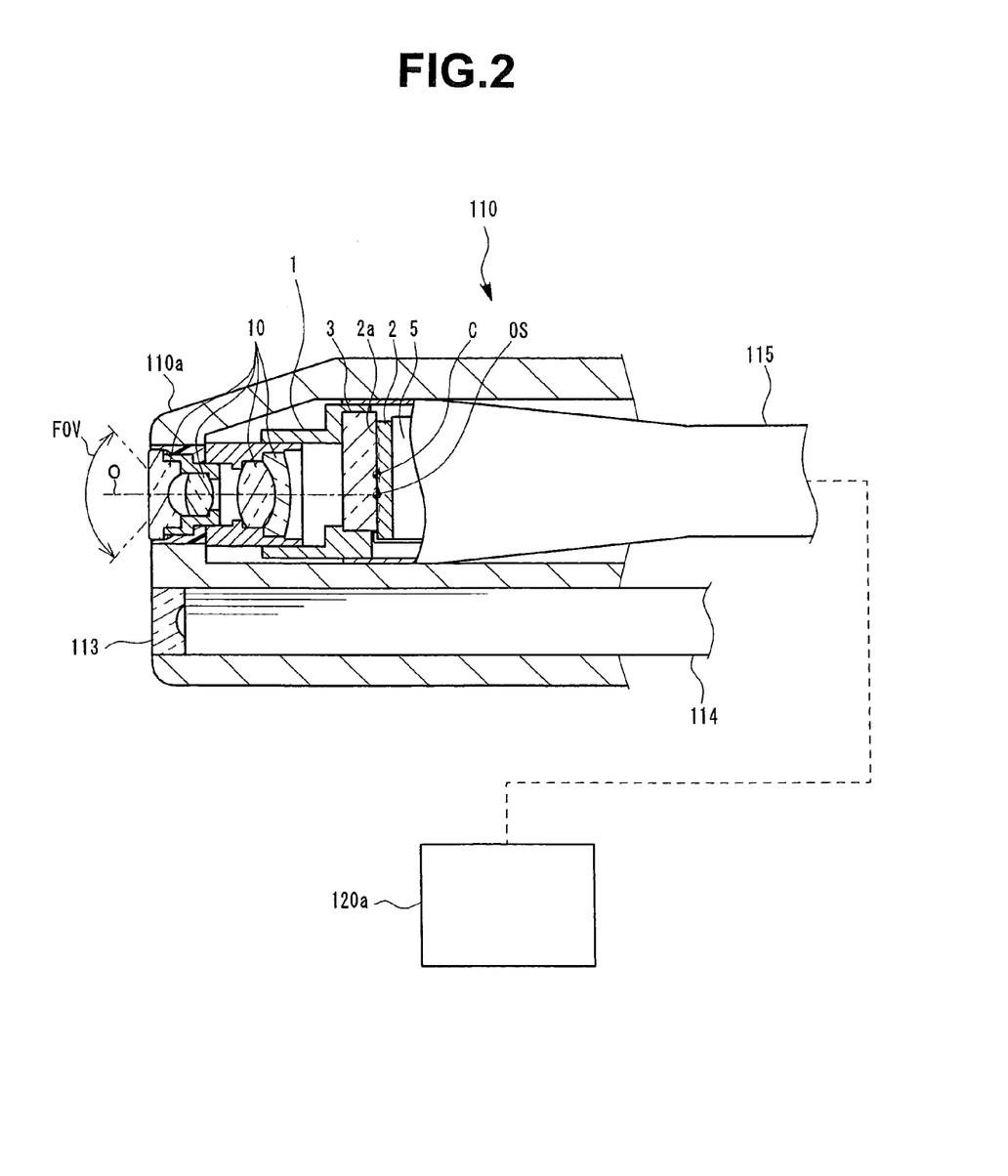
FIG. 2 is a cross-sectional view illustrating a schematic configuration of a distal end portion of the endoscope.

As shown in FIG. 2, the distal end portion 110 is provided with the image pickup unit 1, and an illumination light emitting section 113. Although detailed description will be made later, the image pickup unit 1 is configured by including an image pickup optical system member 10 and an image pickup device 2. A transmission cable 115 such as a coaxial cable is extended from the proximal end side of the image pickup unit 1. In the present embodiment, as one example, the image pickup unit 1 is disposed such that the field of view FOV is directed in the distal end direction of the distal end portion 110. Note that the image pickup unit 1 may be disposed so as to pick up an image of the lateral side of the distal end portion 110.

In addition, a distal end of an optical fiber bundle 114 is disposed at the illumination light emitting section 113. The optical fiber bundle 114 extends from the illumination light emitting section 113 toward the proximal end side of the insertion portion 102.

The operation portion 103 disposed at the proximal end of the insertion portion 102 is provided with an angle operation knob 106 for operating the bending of the bending portion 109. At the proximal end portion of the universal cord 104, an connector section 105 configured to be connectable to an external device 120 is provided. The external device 120 to which the endoscope connector 105 is connected is configured by including a light source section, a camera control unit 120a, and an image display portion 121, for example.

The above-described transmission cable 115 and the optical fiber bundle 114 are inserted through the insertion portion 102, the operation portion 103 and the universal cord 104, and the proximal ends of the transmission cable 115 and optical fiber bundle 114 are disposed at the connector section 105.

The transmission cable 115 is configured so as to electrically connect the image pickup unit 1 and the connector section 105. The connector section 105 is connected to the external device 120, thereby allowing the image pickup unit 1 to be electrically connected to a camera control unit 120a of the external device 120 through the transmission cable 115. Power is supplied from the external device 120 to the image pickup unit 1, and a signal is transmitted and received between the external device 120 and the image pickup unit 1, through the transmission cable 115.

The camera control unit 120a is configured to generate a video based on a signal outputted from the image pickup unit 1 and output the generated video to the image display portion 121. That is, in the present embodiment, an optical image picked up by the image pickup unit 1 is displayed as a video on the display portion 121. Note that a part of or entire of the camera control unit 120a and image display portion 121 may be configured integrally with the endoscope 101.

Furthermore, the optical fiber bundle 114 is configured to transmit the light emitted from a light source device included in the external device 120 to the illumination light emitting section 113 of the distal end portion 110. The illumination light emitting section 113 is configured to emit the light entered from the optical fiber bundle 114 and illuminate the field of view of the image pickup unit 1. Note that the light source device may be disposed in the operation portion 103 or the distal end portion 110 of the endoscope 101.

Figure 3:
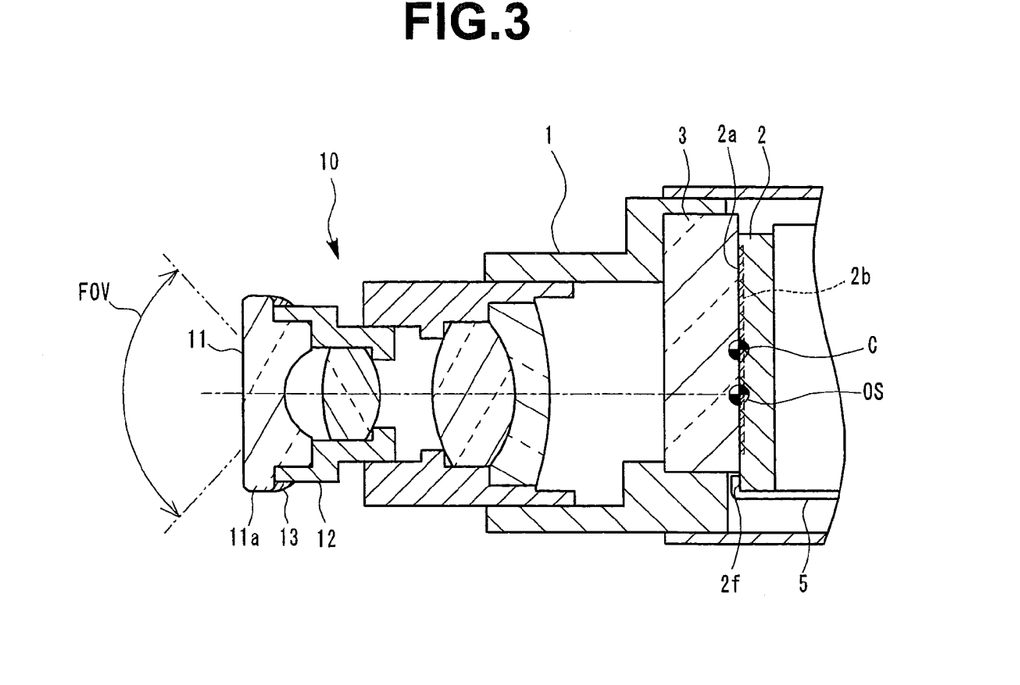
FIG. 3 is a partial cross-sectional view of an image pickup unit.

Next, detailed configuration of the image pickup unit 1 will be described. As described above, the image pickup unit 1 is configured by including the image pickup optical system member 10 and the image pickup device 2. In addition, the image pickup unit 1 includes a peripheral circuit section 5 as an electronic circuit which is electrically connected to the image pickup device 2. The transmission cable 115 is electrically connected to the image pickup device 2 through the peripheral circuit section 5.

The image pickup optical system member 10 includes optical elements such as a lens, a prism, a filter, and the like, and is configured to form an image of an object of shooting. In the present embodiment, as one example, the image pickup optical system member 10 is constituted of a plurality of lenses disposed on a linear optical axis O. Note that the image pickup optical system member 10 may include a prism or a mirror and may be configured such that the optical axis O is curved. Hereinafter, it is supposed that a direction toward the object of shooting (object side) along the optical axis O is called an object side, and a direction opposite to the object side is called an image side.

The image pickup device 2 is disposed on the image side of the image pickup optical system member 10. The image pickup device 2 is arranged such that the light-receiving surface 2a on which a plurality of pixels including light-receiving elements are disposed is oriented toward the image pickup optical system member 10. A cover glass 3 is disposed on the light-receiving surface 2a of the image pickup device 2.

The image pickup device 2 is configured to be able to convert an optical image formed by the image pickup optical system member 10 into an electric signal. The image pickup device 2 is an image sensor which is generally called as a CCD or a CMOS image sensor, and detailed description on the detailed working principle and the like will be omitted.

Figure 4:
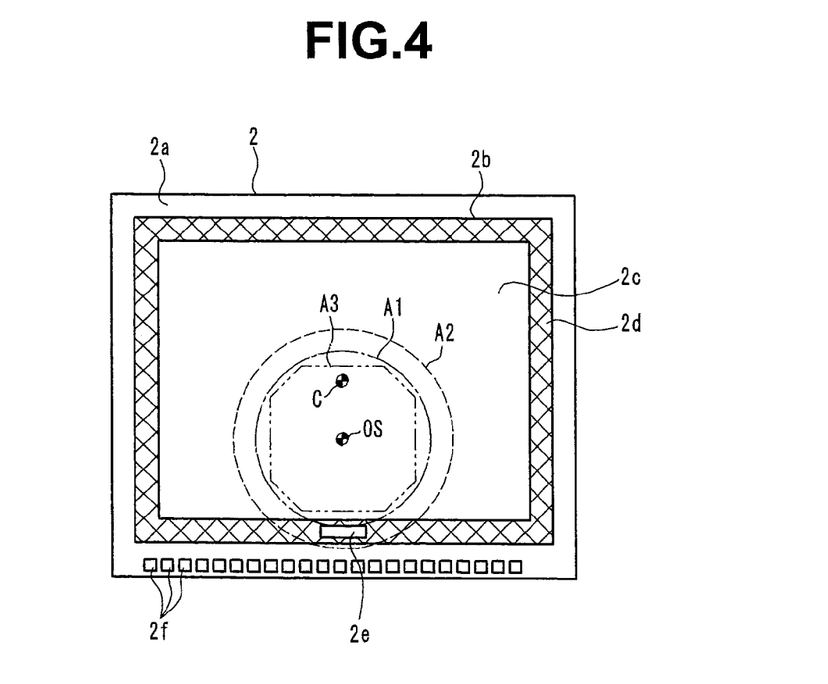
FIG. 4 is a front view of a light-receiving surface of the image pickup device viewed from the light-receiving surface side.

FIG. 4 is a front view of the image pickup device 2 viewed from the light-receiving surface 2a side. As shown in FIG. 4, the image pickup device 2 according to the present embodiment is substantially a rectangular shape when viewed from the light-receiving surface 2a side. On the light-receiving surface 2a side of the image pickup device 2, a pixel forming region 2b, as a rectangular region, in which a plurality of pixels are formed in a predetermined alignment is provided.

In addition, a plurality of metal pads 2f for electrically connecting the image pickup device 2 and the peripheral circuit section 5 are formed outside the pixel forming region 2b on the light-receiving surface 2a side of the image pickup device 2. The metal pads 2f and the peripheral circuit section 5 are electrically connected to each other by wire bonding using a metal wire, for example.

Note that, in the present embodiment, the metal pads 2f are provided on the light-receiving surface 2a side of the image pickup device 2, but not limited thereto, and may be provided on the rear surface side of the light-receiving surface 2a of the image pickup device 2. The metal pads provided on the rear surface side of the light-receiving surface 2a of the image pickup device 2 are formed by BGA (Ball Grid Array) or LGA (Land Grid Array) provided at through electrodes which penetrate from the light-receiving surface 2a which is located outside the pixel forming region 2b of the image pickup device 2 to the rear surface side, for example.

In the present embodiment, the metal pads 2f are arranged along one of the long sides of the image pickup device 2 having a substantially rectangular outer shape, as an example. That is, in the present embodiment, the metal pads 2f are arranged on only one side in a predetermined one direction of the image pickup device 2. Note that the arrangement configuration of the metal pads 2f is not limited to the one disclosed in the present embodiment, but metal pads may be arranged along two sides of the image pickup device 2, for example, or may be arranged along four sides of the image pickup device 2, for example.

The cover glass 3 is disposed on the light-receiving surface 2a of the image pickup device 2 so as to cover the pixel forming region 2b. The cover glass 3 is adhered onto the light-receiving surface 2a of the image pickup device 2 with ultraviolet cure adhesive, for example.

Next, detailed configuration of the pixel forming region 2b of the image pickup device 2 will be described. As shown in FIG. 4, the pixel forming region 2b is configured by including an effective pixel region 2c and an optical black region 2d provided at the outer peripheral portion of the effective pixel region 2c. In addition, a phase reference pixel region 2e is provided in the optical black region 2d. In FIG. 4, the optical black region 2d is shown by a reticular hatching.

The effective pixel region 2c is a region in which the light from the image pickup optical system member 10 can be incident into the pixels disposed in the effective pixel region 2c. That is, the image pickup device 2 outputs an electric signal corresponding to the optical image formed in the effective pixel region 2c by the image pickup optical system member 10. FIG. 4 illustrates a center C of the effective pixel region 2c. In the present embodiment, the effective pixel region 2c is rectangular shape, and the center C of the effective pixel region 2c is a point at which the diagonal lines of the rectangular-shaped effective pixel region 2c intersect.

The optical black region 2d is a region in which a light-shielding film such as an aluminum film that shields incidence of the light into the pixels disposed in the optical black region 2d is formed on the pixels. The electric signals outputted from the pixels which are covered with the light-shielding film in the optical black region 2d are used for calculating an optical black level.

Note that the configuration of the optical black region 2d is not limited to the configuration in which the optical black region is disposed so as to surround the entire periphery outside the effective pixel region 2c, but the optical black region may be disposed outside of the one side, two sides or three sides of the effective pixel region 2c, for example.

One or a plurality of phase reference pixel regions 2e are disposed at a predetermined position in the optical black region 2d located outside the effective pixel region 2c. The phase reference pixel region 2e is a region including one or a plurality of pixels at a predetermined position, and a signal outputted from a pixel in the phase reference pixel region 2e can be used as a reference for video phase adjustment when a video based on the signal outputted from the image pickup unit 1 is generated in the camera control unit 120a to which the image pickup unit 1 is connected. For example, a signal outputted from a pixel in the phase reference pixel region 2e is used as references for the sampling timing adjustment with respect to the phase and the video display position adjustment in generating the video, which are performed by a sampling circuit, not shown, at the time of adjusting the phase of the video signal outputted from the image pickup unit 1.

The phase reference pixel region 2e is a region in which the light-shielding film is not formed on the predetermined one or a plurality of pixels and the light from the image pickup optical system member 10 side can be incident into the pixels in the optical black region 2d. The electric signal or signals outputted from the pixel or pixels in the phase reference pixel region 2e of the image pickup device 2 in the state where the light is incident into the phase reference pixel region 2e of the image pickup device 2 are different from the electric signals of the optical black level which are outputted from the pixels around the phase reference pixel region in the optical black region 2d. Since the position of the phase reference pixel region 2e is a known predetermined position, it is possible to perform video phase adjustment such as the sampling timing adjustment and the video display position adjustment in the camera control unit 120a by using the signal or signals outputted from the pixel or pixels in the phase reference pixel region 2e in the light-receiving state.

In the present embodiment, as one example, the phase reference pixel region 2e is provided on the side in the predetermined one direction, where the metal pads 2f are formed, among the four sides of the optical black region 2d surrounding the outer periphery of the effective pixel region 2c.

Next, description will be made on the positional relationship between the image pickup optical system member 10 and the image pickup device 2 in the image pickup unit 1 according to the present embodiment. FIG. 4 shows an image circle A1, a transmitted light reaching region A2, and a video display region A3, which are regions defined on the light-receiving surface 2a depending on the specifications of the image pickup optical system member 10 and the image pickup device 2 and the positional relationship therebetween.

In this embodiment, the image circle A1 indicates a range in which aberration of the image is within a predetermined acceptable range in the image formed on the light-receiving surface 2a by the image pickup optical system member 10. In FIG. 4, the image circle A1 is shown by the one-dot chain line. In the present embodiment, as one example, the image circle A1 is substantially a circle shape, and the center of the image circle A1 substantially coincides with an intersection point OS at which the optical axis O and the effective pixel region 2c on the light-receiving surface 2a intersect. Note that the shape of the image circle A1 is determined depending on the configuration of the image pickup optical system member 10 and not limited to a circle shape.

In addition, the transmitted light reaching region A2 indicates a range in which the light which is incident into the image pickup optical system member 10 from the object side and transmitted through the image pickup optical system member 10 to be emitted toward the image side can reach the light-receiving surface 2a. In FIG. 4, the transmitted light reaching region A2 is shown by the dashed line. Generally, the transmitted light reaching region A2 is a range which includes the image circle A1 and which is larger than the image circle A1. Note that the transmitted light reaching region A2 is substantially circle shape in the present embodiment. However, the shape of the transmitted light reaching region A2 is determined depending on the configuration of the image pickup optical system member 10 and is not limited to a circle shape. In addition, the shape of the transmitted light reaching region A2 is not limited to a shape which is substantially similar to the shape of the image circle A1.

The video display region A3 is a region in the image circle A1, and indicates a region in which the video in the range displayed on the image display device 121 is picked up by the image pickup unit 1. That is, the field of view FOV of the endoscope 101 coincides with the image formed in the video display region A3 by the image pickup optical system member 10. In FIG. 4, the video display region A3 is shown by the two-dot chain line.

The shape and the size of the video display region A3 is determined so as to fit inside the effective pixel region 2c and also fit inside the image circle A1. In the present embodiment, the shape of the video display region A3 has an octagonal shape formed by cutting off corners of a square, as one example. Note that the shape of the video display region A3 is not limited to the shape disclosed in the present embodiment, but may be a rectangular shape or a circular shape.

The video display region A3 may have a configuration in which a method of driving a part of pixels among all the pixels of the image pickup device 2 is adopted, or a configuration in which a method of generating a video by using a part of electric signals outputted from all the pixels of the image pickup device 2 is adopted.

As shown in FIG. 4, in the present embodiment, the position of the intersection point OS is determined such that the phase reference pixel region 2e is positioned inside the transmitted light reaching region A2 of the image pickup optical system member 10. That is, the relative position between the image pickup optical member 10 and the image pickup device 2 is determined such that the light incident from the object side to the image pickup optical system member 10 and transmitted through the image pickup optical system member 10 can reach the phase reference pixel region 2e. Note that the phase reference pixel region 2e may be positioned inside the image circle A1.

Specifically, in the present embodiment, the area of the image circle A1 of the image pickup optical system member 10 is smaller than the area of the effective pixel region 2c in the image pickup unit 1. The intersection point OS at which the optical axis O of the image pickup optical system member 10 and the effective pixel region 2c intersect is arranged at a position shifted in the direction closer to the phase reference pixel region 2e with respect to the center C of the effective pixel region 2c such that the phase reference pixel region 2e is positioned in the transmitted light reaching region A2.

As described above, the image pickup unit 1 according to the present embodiment is configured by including the image pickup device 2 and the image pickup optical system member 10 having the image circle A1 narrower than the effective pixel region 2c of the image pickup device 2. The image pickup device 2 has the phase reference pixel region 2e including a pixel or pixels which output the signals used for performing video phase adjustment, outside the effective pixel region 2c. The image pickup optical system member 10 is disposed in such a manner that the intersection point OS at which the optical axis O intersects with the effective pixel region 2c is shifted to be located at the position closer to the phase reference pixel region 2e with respect to the center C of the effective pixel region 2c so as to allow the light transmitted through the image pickup optical system member 10 to reach the phase reference pixel region 2e.

In the image pickup unit 1 according to the present embodiment, the image pickup optical system member 10 can be formed in a compact size by making the image circle A1 of the image pickup optical system member 10 narrower than the effective pixel region 2c of the image pickup device 2.

Note that the present embodiment provides the configuration in which the area of the image circle A1 is smaller than the area of the effective pixel region 2c. However, the present invention is not limited to such a configuration, and the image pickup optical system member 10 can be formed in a compact size by a configuration in which, when the intersection point OS which is substantially the center of the image circle A1 is arranged at the center C of the effective pixel region 2c, the transmitted light reaching region A2 does not reach the phase reference pixel region 2e, that is, the radius of the transmitted light reaching region A2 is made shorter than the distance between the center C of the effective pixel region 2c and the part of the phase pixel region 2e which is farthest from the center C.

Note that the image pickup unit 1 of the endoscope 101 is electrically connected to the camera control unit 120a through the relatively long transmission cable 115 of ten and several centimeters to several meters, for example. Therefore, the communication state between the image pickup unit 1 and the camera control unit 120a greatly varies due to the variations in the length and electrical properties of the transmission cable 115 and the variation in the electrical performances of the incorporated electronic components. Accordingly, in the image pickup unit 1 of the endoscope 101, video phase adjustment is required to be performed in the state where the image pickup unit is completed so as to be able to be accommodated into the endoscope 101, that is, in the state where the transmission cable 115 is connected to the image pickup unit 1.

Therefore, in the present embodiment, the intersection point OS at which the optical axis O of the image pickup optical system member 10 and the effective pixel region 2c intersect is arranged at a position shifted from the center C of the effective pixel region 2c in the direction closer to the phase reference pixel region 2e, thereby enabling the light to be incident into the phase reference pixel region 2e at the time of video phase adjustment even in the image pickup unit 1 having a compact image pickup optical system member 10. According to the configuration, in the present embodiment, the video phase adjustment can be performed in the image pickup unit 1 having the compact image pickup optical system member 10 without providing a timing generator in the vicinity of the image pickup device 2. As a result, the size of the peripheral circuit section 5 of the image pickup device 2 of the image pickup unit 1 can be reduced. In addition, according to the present embodiment, the video phase adjustment can be performed in the image pickup unit 1 in the state where the image pickup optical system member 10, the image pickup device 2 and the transmission cable 115 are assembled.

Furthermore, in the image pickup unit 1 according to the present embodiment, the phase reference pixel region 2e is disposed at a position closer to the metal pads 2f of the image pickup device 2 than the center C of the effective pixel region 2c (the side on which the metal pads 2f are formed, with respect to the center C). That is, the image pickup optical system member 10 is disposed such that the intersection point OS at which the optical axis O and the effective pixel region 2c intersect is located so as to shift toward the side on which the metal pads 2f are formed, with respect to the center C of the effective pixel region 2c. The side of the image pickup device 2, on which the metal pads 2f are formed, generally protrudes outward more than other three sides of the image pickup device 2 with respect to the pixel forming region 2b. In the present embodiment, the phase reference pixel region 2e and the intersection point OS are arranged closer to the direction of the side protruding outward most with respect to the pixel forming region 2b, among the four sides of the rectangular image pickup device 2. According to the configuration, the optical axis O of the image pickup optical system member 10 is shifted from the center C of the effective pixel region 2c to be closer to the side on which the metal pads 2f of the image pickup device 2 are formed, thereby capable of reducing the amount by which the image pickup optical system member 10 protrudes more in a direction perpendicular to the optical axis O than the outer diameter of the image pickup device 2. In other words, it is possible to reduce an increase in the projection area on a plane perpendicular to the optical axis O of the image pickup unit 1 in the case where the intersection point OS at which the optical axis O of the image pickup optical system member 10 and the effective pixel region 2c intersect is arranged so as to shift from the center C of the effective pixel region 2c.

In addition, in the endoscope 101 having the compact image pickup unit 1 according to the present embodiment, it is possible to reduce the size of the distal end portion 110 of the insertion portion 102. In addition, as shown in FIG. 2, when the direction in which the intersection point OS at which the optical axis O of the image pickup optical system member 10 and the effective pixel region 2c intersect is shifted is supposed to be an inward of the diameter direction of the distal end portion 110, the image pickup optical system member 10 can be disposed inward in the diameter direction of the distal end portion 110, compared with the case where the intersection point OS and the center C coincides with each other. Therefore, a tapered portion 110a, the diameter of which is reduced toward the distal end, can be formed at the distal end portion 110 of the insertion portion 102 in the endoscope 101 according to the present embodiment. Providing the tapered portion 110a facilitates the insertion operation of the insertion portion 102.

Note that, in the image pickup optical system member 10 in the present embodiment, a first lens 11 located on the most object side and a first lens frame 12 which holds the first lens 11 are fixed to each other not only by adhesive but also by soldering 13.

Specifically, as shown in FIG. 3, a flange portion 11a which protrudes outward in the diameter direction is formed on the side surface of the first lens 11. The flange portion 11a is provided at a position where the light beam in the field of view FOV of the image pickup optical system member 10 does not transmit, and the flange portion does not have an optical function of the first lens 11. The outer diameter of the flange portion 11a is equal to or larger than the outer diameter of the first lens frame 12. A metallic film is deposited on the side surface and the surface facing the image side of the flange portion 11a over the entire circumferential direction.

Then, the metallic film of the flange portion 11a and the first lens frame 12 are fixed to each other by the soldering 13 over the entire circumferential direction. Thus, the flange portion 11a of the first lens 11 and the first lens frame 12 are fixed to each other by the soldering in the circumferential direction, thereby increasing the air-tightness between the first lens 11 and the first lens frame 12 and preventing moisture from entering the image pickup unit 1.

In addition, the metallic film is generally shiny. Therefore, when the metallic film is provided on the side surface of the lens, the metallic film may become a source of generation of flare. However, in the present embodiment, the metallic film is formed on the flange portion 11a protruded outward in the diameter direction from the first lens 11, thereby keeping the metallic film away from the path of the light beam in the field of view FOV of the image pickup optical system member 10 and preventing the generation of flare.

Figure 5:
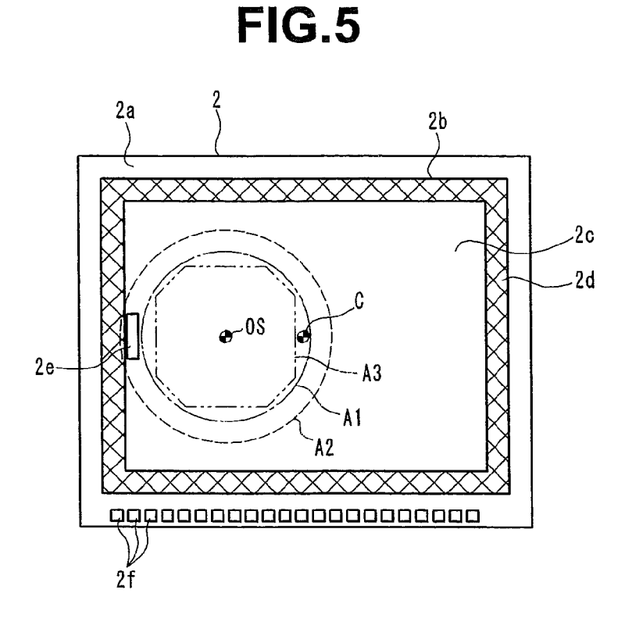
FIG. 5 is a front view of the light-receiving surface of the image pickup device viewed from the light-receiving surface side.

Note that the phase reference pixel region 2e is provided at a predetermined position in the optical black region 2d in the present embodiment. However, the position of the phase reference pixel region 2e is not limited to the position disclosed in the present embodiment. For example, the phase reference pixel region 2e may be provided at a predetermined position which is in the effective pixel region 2c and outside the video display region A3. FIG. 5 illustrates an example in which the phase reference pixel region 2e is provided along the one side of the rectangular effective pixel region 2c so as to be located at a position which is in the effective pixel region 2c and outside the video display region A3.

In addition, the image pickup optical system member 10 according to the present embodiment is configured such that the area of the image circle A1 is smaller than the area of the effective pixel region 2c. However, the relationship between the size of the image pickup optical system member 10 and the size of the image pickup device 2 is not limited to the one disclosed in the present embodiment. It is only necessary that the image pickup optical system member 10 has a configuration in which the radius of the transmitted light reaching region A2 is shorter than the distance between the center C of the effective pixel region 2c and the part of the phase pixel region 2e which is farthest from the center C.

For example, as shown in FIG. 5, in the case of the image pickup device 2 including the phase reference pixel region 2e along the short side of the rectangular effective pixel region 2c, the image pickup optical system member 10 may have a configuration in which the diameter of the image circle A1 is shorter than the long side of the rectangular outer shape of the effective pixel region 2c.

Second Embodiment

Hereinafter, description will be made on the second embodiment of the present invention. The present embodiment is different from the first embodiment in the configuration of the image pickup optical system member 10. Accordingly, only the points different from the first embodiment will be described. The same components as those in the first embodiment are attached with the same reference numerals, and description thereof will be omitted as appropriate.

Figure 6:
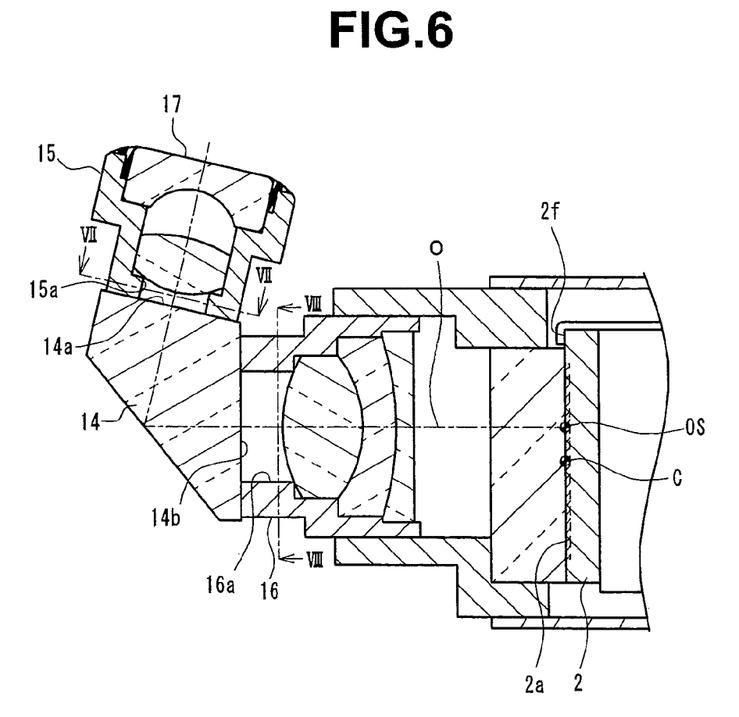
FIG. 6 is a partial cross-sectional view of an image pickup unit according to a second embodiment.

In the above-described first embodiment, the optical axis O of the image pickup optical system member 10 is linear shape, and as shown in FIG. 6, the image pickup optical system member 10 according to the present embodiment is provided with a prism 14 and the optical axis O is bent halfway.

The image pickup optical system member 10 according to the present embodiment has an image circle A1 narrower than the effective pixel region 2c of the image pickup device 2 similarly as in the first embodiment. Then, the image pickup unit 1 according to the present embodiment is configured such that the intersection point OS at which the optical axis O of the image pickup optical system member 10 and the effective pixel region 2c intersect is arranged at a position shifted from the center C of the effective pixel region 2c in the direction closer to the phase reference image region 2e and the phase reference pixel region 2e is positioned in the transmitted light reaching region A2.

Note that, in the present embodiment, the metal pads 2f, the phase reference pixel region 2e and the intersection point OS are provided on the upper side than the center C of the effective pixel region 2c on the paper surface in FIG. 6 (in the direction toward the object side along the optical axis O), but not limited to such a configuration. The metal pads 2f, the phase reference pixel region 2e, and the intersection point OS may be provided on the lower side than the center C of the effective pixel region 2c on the paper surface in FIG. 6.

It is needless to say that the same effects as those in the first embodiment can be obtained also in the present embodiment configured as such. That is, according to the present embodiment, it is possible to reduce the size of the image pickup optical system member 10. In addition, in the image pickup unit 1 having a compact image pickup optical system member 10, the video phase adjustment can be performed without providing a timing generator in the vicinity of the image pickup device 2, thereby capable of reducing the size of the peripheral circuit section 5. Furthermore, it is possible to reduce the size of the distal end portion 110 of the insertion portion 102 of the endoscope 101 including the image pickup unit 1.

Note that, in the image pickup optical system member 10 according to the present embodiment, as one example, the first lens frame 15 which holds the lens located closer to the object side than the prism 14 and the second lens frame 16 which holds the lens located closer to the image side than the prism 14 are fixed to an incident surface 14a and an emission surface 14b of the prism 14, respectively, with adhesive.

Figure 7:
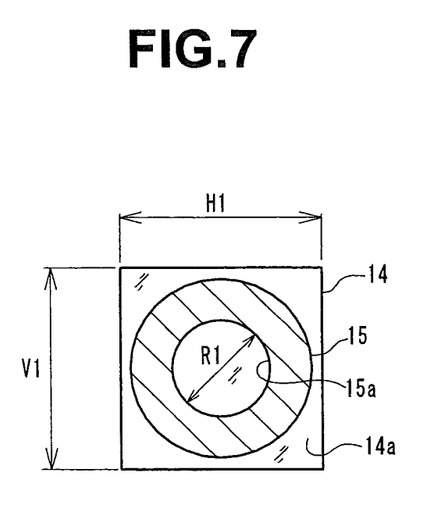
FIG. 7 is a cross-sectional view along VII-VII line of FIG. 6.
Figure 8:
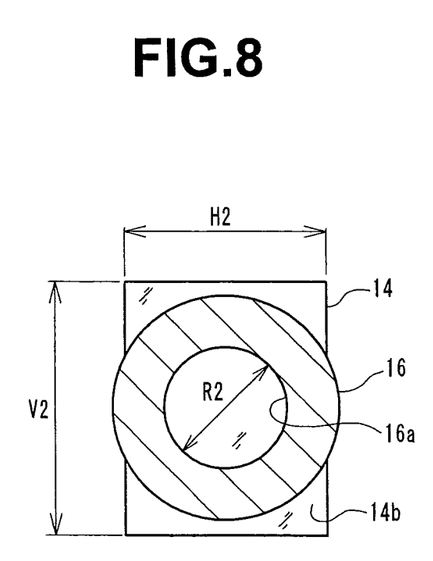
FIG. 8 is a cross-sectional view along VIII-VIII line of FIG. 6.

FIG. 7 is a cross-sectional view (viewed in the direction of the arrow VII in FIG. 6) for comparing the shape of the incident surface 14a of the prism 14 with the shape of the adhering surface of the first lens frame 15 adhered to the incident surface 14a. In addition, FIG. 8 is a cross-sectional view (viewed in the direction of the arrow VIII in FIG. 6) for comparing the shape of the emission surface 14b of the prism 14 and the shape of the adhering surface of the second lens frame 16 adhered to the emission surface 14b.

The first lens frame 15 is substantially a cylindrical shape and an inner diameter R1 of a hole 15a which opens on the adhering surface adhered to the incident surface 14a is set to be smaller than a smaller one of a lateral dimension H1 and a longitudinal dimension V1 of the rectangular incident surface 14a. The first lens frame 15 is adhered to the incident surface 14a such that the entirety of the hole 15a which opens on the adhering surface fits within the incident surface 14a. In other words, the hole 15a of the first lens frame 15 is occluded by the incident surface 14a.

Similarly, the second lens frame 16 is substantially a cylindrical shape, and an inner diameter R2 of a hole 16a which opens on the adhering surface adhered to the emission surface 14b is set to be smaller than a smaller one of a lateral dimension H2 and a longitudinal dimension V2 of the rectangular emission surface 14b. The second lens frame 16 is adhered to the emission surface 14b such that the entirety of the hole 16a which opens on the adhering surface fits within the emission surface 14b. In other words, the hole 16a of the second lens frame 16 is occluded by the emission surface 14b.

The hole 15a and the hole 16a of the first lens frame 15 and the second lens frame 16 as cylindrical lens frames which respectively hold lenses, are occluded by adhering the lens frames to the prism 14, thereby capable of preventing moisture from entering the image pickup unit 1 from the holes 15a and 16a. Accordingly, it is not necessary to cover the periphery of the prism 14 with another member in order to prevent moisture from entering the image pickup unit 1, thereby capable of reducing the size of the image pickup unit 1.

Figure 9:
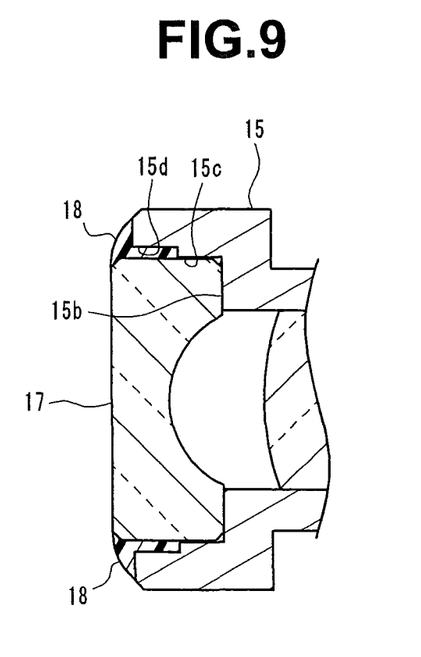
FIG. 9 is a partial cross-sectional view of a first lens and a first lens frame.

Next, description will be made on the configuration in which the first lens 17 located on the most object side is fixed to the first lens frame 15 which holds the first lens 17 with the adhesive in the image pickup optical system member 10 according to the present embodiment.

As shown in FIG. 9, the first lens 17 is fixed to the first lens frame 15 by an adhesive 18 being filled around the lens in a state where the lens is dropped from the object side into a recessed portion 15b which opens on the object side of the first lens frame 15.

The recessed portion 15b is configured by a small-diameter portion 15c having an inner diameter to which the outer diameter of the first lens 17 is fitted with a predetermined space left, and a large-diameter portion 15d which has a diameter larger than that of the small-diameter portion 15c. In the present embodiment, the large-diameter portion 15d is disposed on the more object side than the small-diameter portion 15c, that is, on the opening side.

In the present embodiment thus configured, the positioning of the first lens 17 in the diameter direction is performed with high accuracy by the fitting between the small-diameter portion 15c on the back side (image side) of the recessed portion 15b and the first lens 17. In addition, since the space between the large-diameter portion 15d and the first lens 17 is larger than the space between the small-diameter portion 15c and the first lens 17, a sufficient amount of adhesive 18 is stably filled into the large space. In the present embodiment, the first lens frame 15 and the first lens 17 are firmly adhered to each other, thereby capable of preventing moisture from entering inside of the image pickup unit 1 from the space between the first lens 17 and the first lens frame 15 while performing positioning of the first lens 17 with high accuracy.

Figure 10:
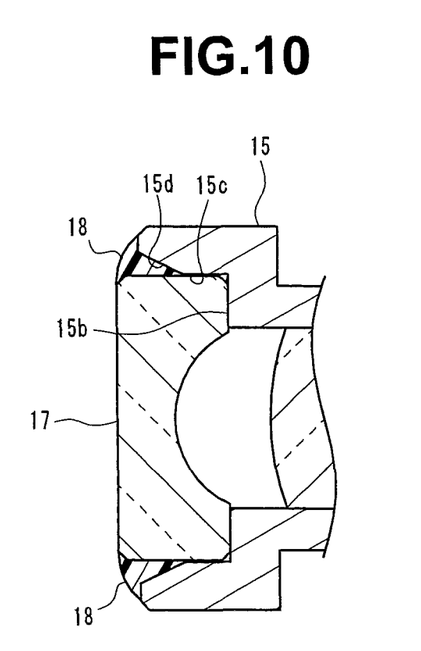
FIG. 10 is a partial cross-sectional view of a first lens and a first lens frame according to a first modified example.

Note that the shape of the recessed portion 15b is not limited to the shape disclosed in the present embodiment. For example, as shown in FIG. 10, the large-diameter portion 15d may have a tapered shape, the diameter of which increases toward the object side (opening side). According to such a configuration, it is possible to increase the amount of the adhesive 18, thereby capable of adhering the first lens frame 15 and the first lens 17 more firmly.

Figure 11:
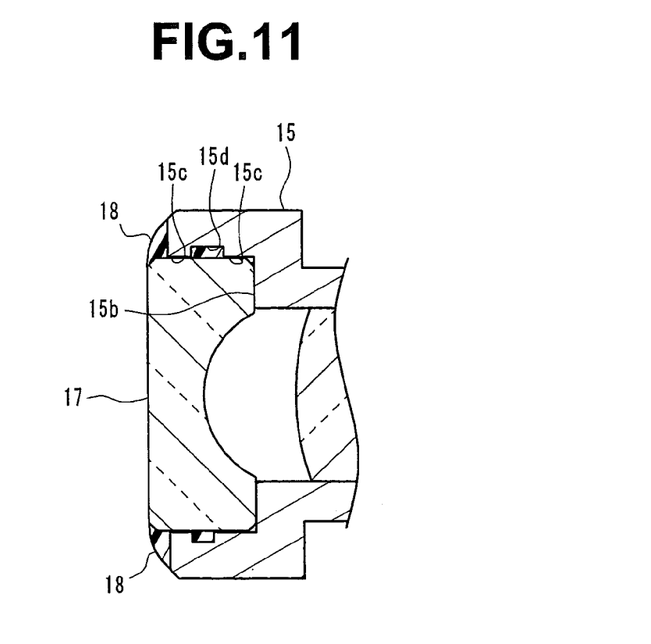
FIG. 11 is a partial cross-sectional view of a first lens and a first lens frame according to a second modified example.
Figure 12:
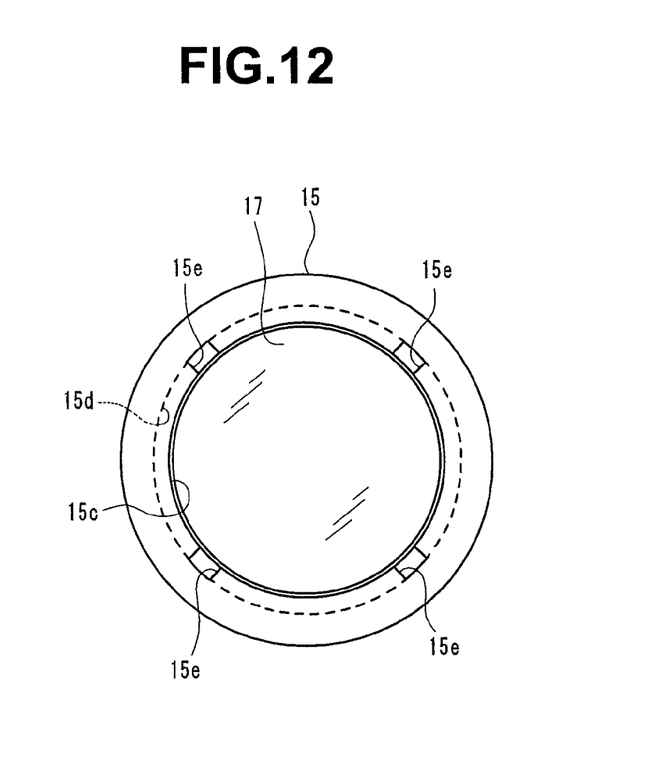
FIG. 12 is a front view of the first lens and the first lens frame according to the second modified example.

In addition, for example, as shown in FIG. 11, the small-diameter portion 15c may be provided both on the image side (back side) and the object side (opening side) of the recessed portion 15b, and the large diameter portion 15d may be provided between the pair of the small-diameter portions 15c. Such a configuration enables the fitting length between the small-diameter portion 15c and the first lens 17 in the optical axis direction to be longer, thereby capable of preventing inclination or shift of the optical axis of the first lens 17 and positioning the first lens frame 17 more accurately. In addition, in this configuration, as shown in FIG. 12, it is preferable to provide a groove portion 15e which extends from the object side end face of the first lens frame 15 to the large diameter portion 15*d*, as shown in FIG. 12. It is possible to easily and stably fill a sufficient amount of the adhesive 18 into the large-diameter portion 15*d* through the groove portion 15*e*.

The present invention is not limited to the above-described embodiments, and can be modified as appropriate within a range not departing from the gist of the invention and scope of the invention which can be interpreted from claims and the whole description, and an image pickup unit and endoscope with such a modification are also included in the technical range of the present invention.

What is claimed is:

1. An image pickup unit comprising:
    an optical system for forming an optical image of an object;
    an image pickup device for converting the optical image into an electric signal, the image pickup device including a pixel forming region in which a plurality of pixels are disposed, the pixel forming region including an effective pixel region, a video display region provided in the effective pixel region, and a phase reference pixel region provided outside the video display region, the phase reference pixel region including pixels disposed therein, the pixels being capable of outputting a signal that is usable for phase adjustment of the video by receiving light; and
    a lens frame for holding a lens included in the optical system;
    a holder for holding the image pickup device and the lens frame, the holder holding the lens frame such that an intersection point at which an optical axis of the optical system intersects the effective pixel region is positioned shifted to a position closer to the phase reference pixel region with respect to a center of the effective pixel region so that light that has transmitted the optical system can reach the phase reference pixel region;
    wherein the optical system has an image circle with an area that is smaller than an area of the effective pixel region of the image pickup device.

2. The image pickup unit according to claim 1, wherein
    the optical system includes a first lens and a second lens disposed in this order from an object side to the image pickup device, and
    the lens frame includes a first lens frame for holding the first lens and a second lens frame for holding the second lens.

3. The image pickup unit according to claim 2, further comprising a prism, wherein the prism includes an incident surface and an emission surface, an emission-side end of the first lens frame is adhered to the incident surface, and an incident-side end of the second lens frame is adhered to the emission surface.

4. An endoscope comprising the image pickup unit according to claim 1.

* * * * *